United States Patent [19]

Glorieux

[11] 3,998,590
[45] Dec. 21, 1976

[54] APPARATUS FOR ASEPTICIZING CONTACT LENS

[76] Inventor: Gilbert Glorieux, 72, rue Achille Viadieu, 31400 Toulouse, France

[22] Filed: Jan. 20, 1975

[21] Appl. No.: 542,679

[30] Foreign Application Priority Data

Feb. 1, 1974  France .............................. 74.04041

[52] U.S. Cl. .................................... 21/89; 21/92; 219/284; 219/439; 339/153
[51] Int. Cl.² .......................................... A61L 3/00
[58] Field of Search ............... 21/89, 92, 119, 120; 219/271, 275, 326, 284, 288, 289, 293, 401, 430, 437, 439; 339/153, 154 R

[56] References Cited

UNITED STATES PATENTS

| | | | |
|---|---|---|---|
| 1,845,432 | 2/1932 | McRae et al. | 21/119 X |
| 2,611,068 | 9/1952 | Wellens | 21/119 X |
| 2,805,454 | 9/1957 | Ihrig | 21/89 X |
| 3,222,499 | 12/1965 | Concin et al. | 219/293 X |
| 3,519,005 | 7/1970 | Krezanoski et al. | 206/5.1 X |
| 3,585,362 | 6/1971 | Hoogesteger et al. | 219/284 X |
| 3,770,113 | 11/1973 | Thomas | 206/5.1 |
| 3,780,260 | 12/1973 | Elsner | 219/284 |
| 3,892,945 | 7/1975 | Lerner | 219/437 |

OTHER PUBLICATIONS

"Denti-Pur", Hygenics Inc., P.O. Box 530262; Miami Shore, Fla. Jan. 16, 1975.

*Primary Examiner*—Morris O. Wolk
*Assistant Examiner*—Arnold Turk
*Attorney, Agent, or Firm*—Robert E. Burns; Emmanuel J. Lobato; Bruce L. Adams

[57] ABSTRACT

A portable, compact device for sterilizing contact lenses consisting of a cell which has a single cylindrical sidewall and a removable cover having two openings for introducing an electrically conductive liquid thereinto. Two electrodes are mounted internally of the cell electrically connected to two external electrical male plugs constructed for electrical connection to an outlet. A container for receiving an asepticizing liquid therein is mounted for joint removal with said cover. The container has an externally threaded neck extending through an opening in the cover and snugly fitting therein. An internally threaded cover closes the container in a liquid-tight manner and holds therein axially in position a lens-holder that has means for removably holding a pair of contact lens thereon and upstanding grip extending externally of the neck for insertion and removal of the lens-holder.

5 Claims, 9 Drawing Figures

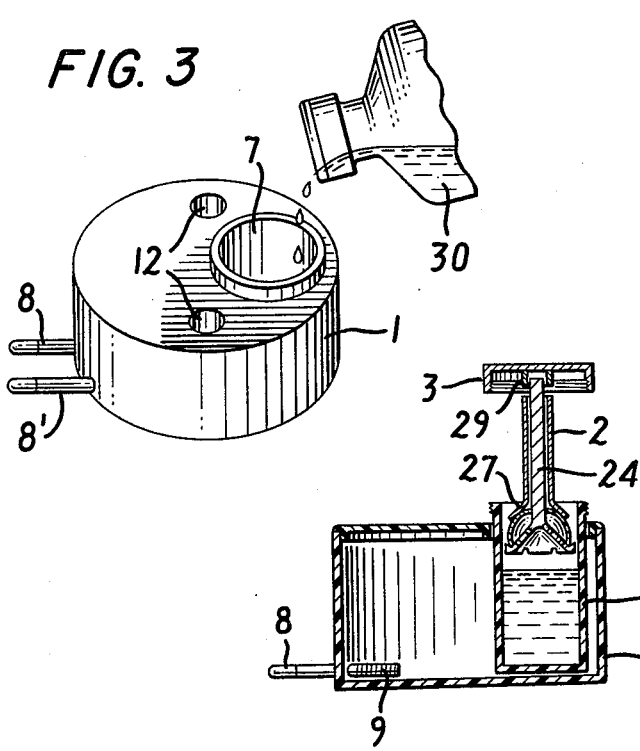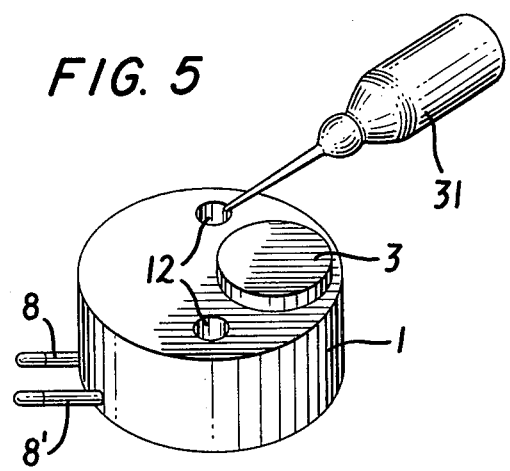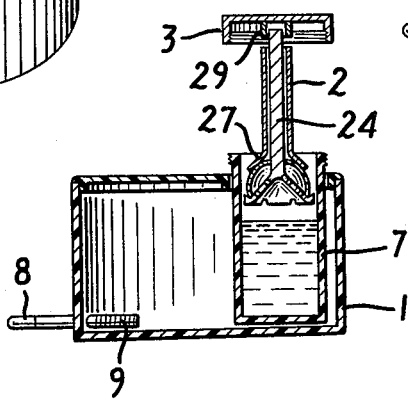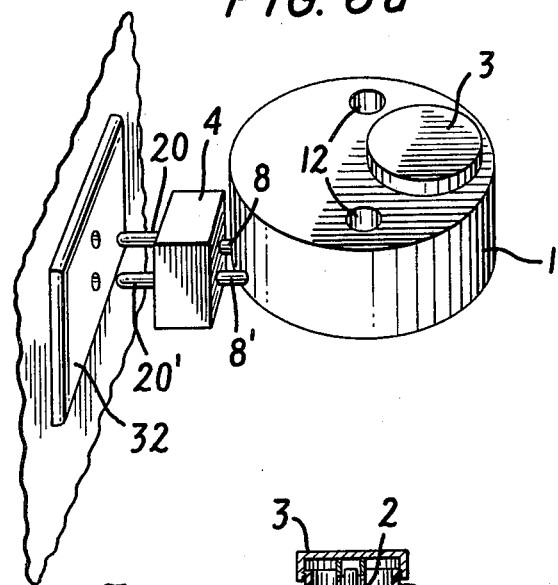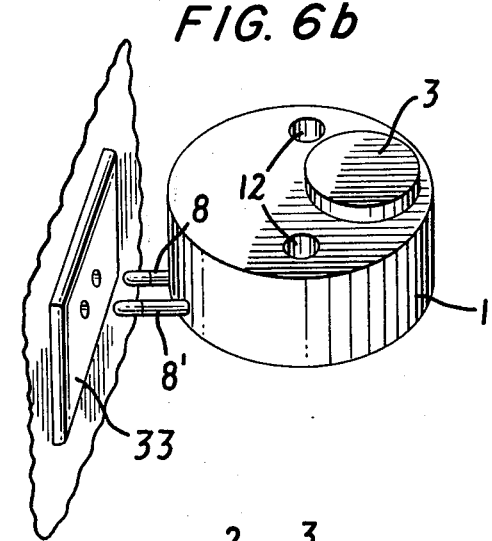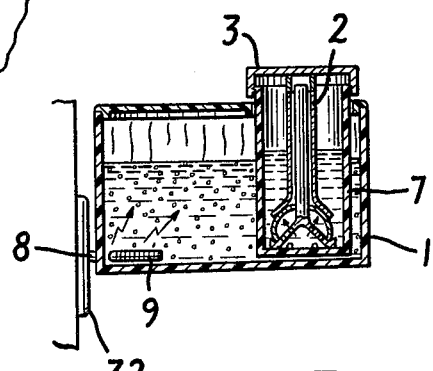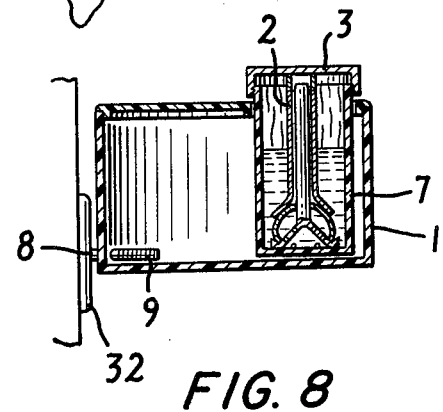

APPARATUS FOR ASEPTICIZING CONTACT LENS

The present invention concerns a sterilizing apparatus for sterilizing optical contact lenses and in particular lenses of soft synthetic material.

Sterilizers are known which comprise an electrical heating resistor and a thermostat and which make it possible to sterilize objects by bringing them to a temperature of about 100° C for a predetermined period of time. When the electrical resistor immersed in a volume of water is placed under voltage the water heats up to its boiling point; when the level of the water is no longer sufficient to cover the resistor entirely, the resistor increases in temperature and the thermostat controlled by the latter causes the disconnecting of the electricity.

However, such apparatus have numerous disadvantages. The most serious is their lack of reliability. A thermostat is a fragile element and it may happen that its operation is defective and it no longer plays its role; the temperature then rises considerably in the apparatus which is seriously damaged and results in the user incurring risks of electrocution or burns; furthermore, the objects to be sterilized are generally themselves damaged when such an accident occurs.

Furthermore, the presence of an electric heating resistor which frequently burns out after a certain period of use makes the life of such apparatus relatively short.

Furthermore, the various parts constituting it (thermostat, resistor, electrical connections, electric wires, etc.) impart a high cost price to this type of apparatus which limits its use among private persons; the apparatus is furthermore cumbersome and inconvenient to use.

There are furthermore sterilizers for surgical instruments, syringes, etc. in which the instrument is immersed in water which is brought to the boiling point by means of electrodes which are under voltage.

However, this type of apparatus cannot be adapted to contact lenses and particularly soft lenses, for two main reasons. First of all, the instruments are immersed in the water, itself which is under voltage, which cannot be permitted in the case of contact lenses which are very fragile objects and must be sterilized in a physiological salt solution in the absence of any electrical current; in addition to the danger of damage, the lenses would be covered by a deposit left by the water which is hydrolyzed upon evaporating. Moreover, the electrical feed of these apparatus must be interrupted manually at the end of the period of sterilization; to be sure this type of apparatus enjoys a safety element in case one forgets to disconnect the current since the total evaporation of the water will finally cause the interruption of the current and avoid the serious accidents to the apparatus referred to above. However, this element of safety which is of interest for surgical elements of steel or resistant material which can stay in a non-liquid hot atmosphere, it is of no use for fragile contact lenses which must remain at all times immersed in the sterilizing liquid during their heating since otherwise they would be damaged; furthermore, in this type of apparatus the deposit which forms on the lenses after complete evaporation of the water is too large to permit utilizing this safety as the procedure for the normal disconnecting of the apparatus.

The present invention is directed at overcoming these defects and in providing an improved apparatus which, by its very design, makes it possible to sterilize contact lenses in an insulated liquid medium with automatic disconnection at the end of a predetermined period of time and which is safe to use with respect to the danger of electrocution.

Another object of the invention is considerably to reduce the cost of the apparatus so as to permit its purchase by private parties.

Still another object is to provide a light compact apparatus which is very easy to use.

For this purpose, a sterilizing apparatus in accordance with the invention comprises:

a cell of a capacity adapted to receive prior to each sterilization a predetermined dose of an electrically conductive liquid a pair of pins fastened to said cell and protruding from it for the feeding of the apparatus with electricity a pair of electrodes, each electrically connected to one pin of the cell and located within the latter near its bottom so as to be able upon each sterilization to bathe in the dose of liquid poured into said cell;

a watertight container arranged in the cell so as to bathe in the dose of liquid upon each sterilization, said container being provided at its upper portion with a neck having an orifice to receive, on the one hand, a sterilization liquid and, on the other hand, the lenses which are to bathe in said liquid;

a closure cover, fastened to the top of the cell so as to close it, said cover having an opening in which the neck of the container is housed so that the orifice of the container is accessible above the cover;

a removable lens support adapted to be arranged in the container, said support comprising holding means adapted to hold the lenses and gripping means making it possible to grasp the said support so as to position it in the container or withdraw it;

a removable container cap adapted to close the opening of the container and to enclose the support in the said container.

Such an apparatus does not have any of the fragile elements with which certain classical apparatus are provided (thermostat, resistor, etc.) and therefore it is not subject to the defects which said members produce. The liquid of the cell is brought to boiling by the liberation of heat which is caused by the passage through it of the electric current; the dose of liquid poured into the cell is so adjusted that this boiling lasts for the period of time necessary for sterilization, depending on the application contemplated. In the case of contact lenses, this time is about 15 to 20 minutes. At the end of this period of time, the evaporation of the liquid has brought the level of the liquid to below the level of the electrodes and the current is automatically shut off. It should be noted that this disconnecting takes place in the absence of any increase in temperature above the boiling temperature and it depends not on an unreliable physical part but on a physical phenomenon which is inescapable. The lenses held by their support are immersed in the sterilization liquid in particular physiological salt solution, contained in the container; as the latter is closed by its cap and is not under voltage, the level of sterilization liquid is substantially constant and the sterilization takes place without any risk of damaging the lenses and without any deposit being formed on them. Thus such an apparatus, which is of extremely simple design, makes it possible to combine the advantages necessary to permit use in full safety by private persons, namely:

automatic shut-off at the end of a predetermined period of time, without possibility of failure;

sterilization of the lenses in insulated liquid medium without voltage;

heating the liquid under voltage at all times out of the reach of the user;

insertion and removal of the lenses without danger of soiling them.

In accordance with one advantageous embodiment, each electrode is formed of a conductive rod which extends the corresponding pin through the wall of the cell; the latter is made of an electrically insulating synthetic material and the electrodes may be arranged in contact with the bottom of the cell so as to cause the practically complete vaporization of the liquid.

The pins are preferably adapted to assure both the electrical feeding of the apparatus and the mechanical supporting thereof in a suitable position; for this purpose, they are separated from each other by a distance equal to the standardized distance between the two female jacks of a wall socket. These pins will therefore position themselves in a substantially horizontal plane either by direct plugging in a wall socket the jacks of which are located in a horizontal plane or by plugging in a vertical wall socket with the use of a removable adapter with which the apparatus is provided. In both cases, the apparatus is firmly secured to the wall socket in a suitable position.

Other characteristics, purposes and advantages of the invention will become evident from the following description read with reference to the accompanying drawings which show one embodiment of the invention by way of illustration and not of limitation; in the drawings FIG. 1 is an exploded view of an apparatus in accordance with the invention seen in cross section along an axial vertical plane;

FIGS. 3, 4, 5, 6a and 6b, 7 and 8 are diagrams illustrating the operation and manner of use of this apparatus.

Figure 1:
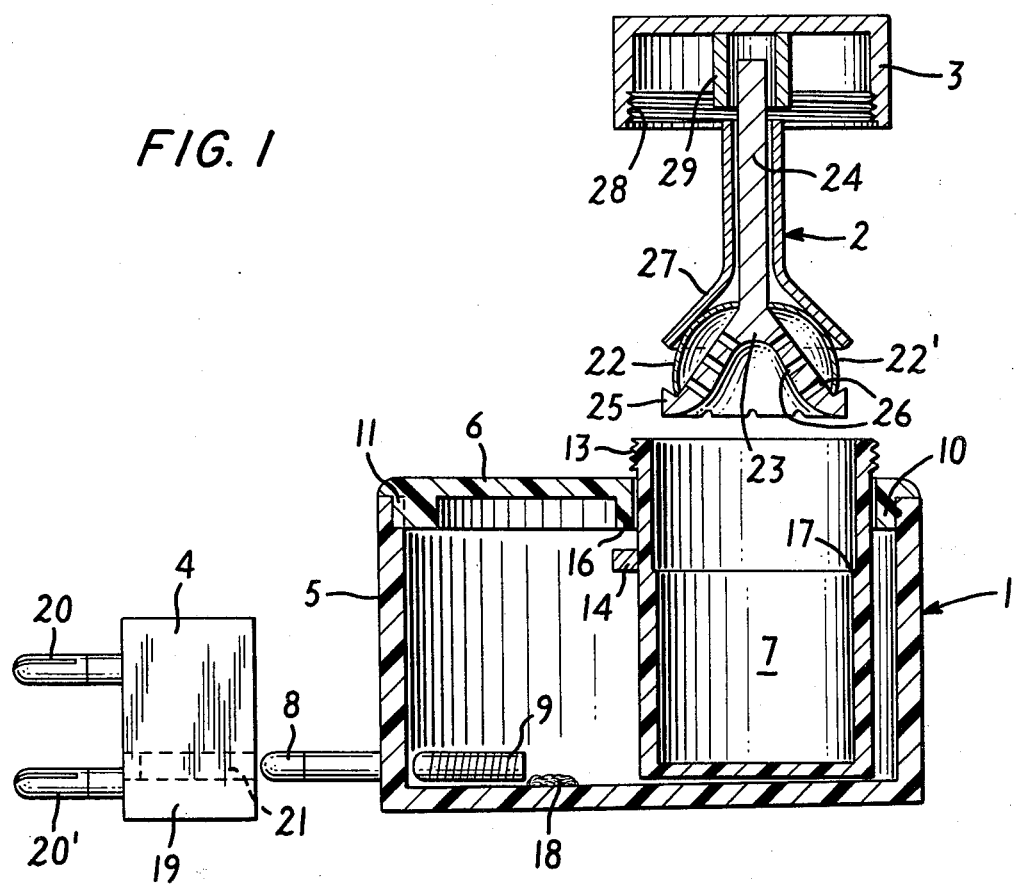

The apparatus shown by way of example in the figures is intended for the sterilizing of optical lenses, in particular hydrophilic flexible lenses. It comprises a main unit 1 and removable parts, namely a lens support 2, a cap 3 and a connecting adapter 4 which can be used possibly for the connecting thereof to an electric wall outlet.

The unit 1 is composed of a cell 5 of electrically insulating synthetic material, of a cover 6 closing the upper face of the cell, of a watertight container 7 arranged in said cell and of a pair of metal pins 8 and 8' fastened to the side wall of the cell which they traverse, each being extended by a rod 9 or 9' which acts as electrode.

The cell 5 is of cylindrical shape and in the normal position of use of the apparatus its side wall is vertical and its bottom inclined slightly towards the electrodes with reference to the horizontal; as will be seen, the cell is held in this position of use by the horizontally plugged pins 8; for this purpose, the distance between the two pins is made equal to the standard distance between the two female jacks of an electric wall outlet.

The electrodes 9 and 9' which form extensions of the pins 8 and 8' are located at the bottom of the cell, so that their end comes into contact with the bottom thereof.

Moreover, the cover 6 which is of circular shape is engaged on the upper part of the cell by means of an annular rim 10 with which it is provided (FIG. 1); this rim is provided on its periphery with a protrusion which, as a result of the elasticity of the material, housed itself in a small groove provided internally in the side wall of the cell. Furthermore, this rim 10 has a spur 11 which, by housing itself in a notch in the cell, locks the cover in a given angular position.

The cover 6 has an opening in which the container 7 is force fitted and, on opposite sides of the latter, two openings such as 12 which serve to feed liquid into the cell and to assure the escape of the vapor formed. Furthermore, these holes make it possible to clean the cell periodically aside from the times when it is in operation by producing a flow of water which enters through one hole and emerges through the other; such a cleaning very effectively eliminates any deposits formed in the cell.

The container 7 is formed of a cylindrical dish having an upper neck which protrudes above the cell; this neck is provided with a thread 13. Moreover the container is provided with protective fins 14 which place themselves within the cell under each hole 12 so as to mask the electrodes 9 and 9' and avoid any possibility of contact with them; these fins for instance eliminate any risk of electrocution for children who might be tempted to introduce pins through the holes 12.

Figure 2:
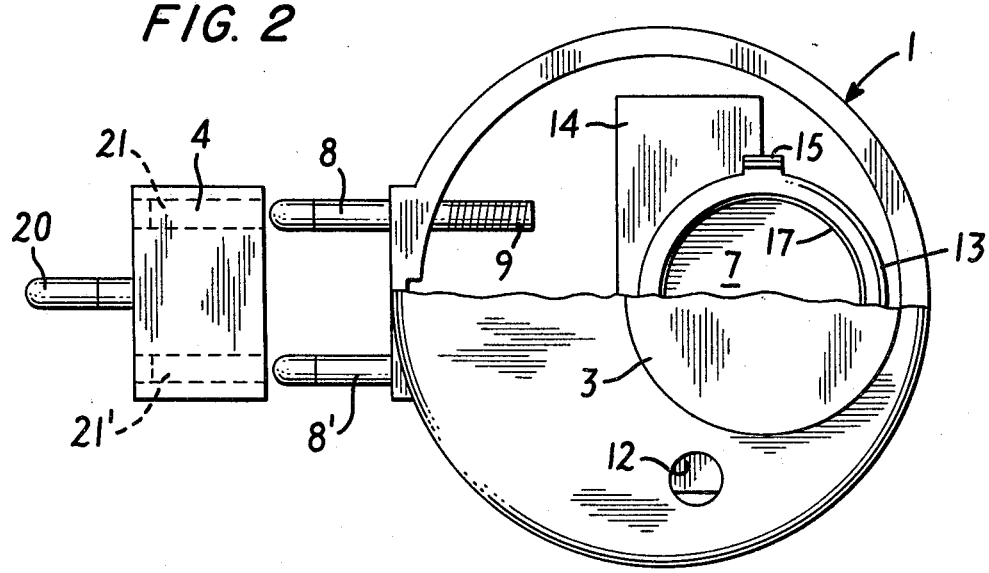
FIG. 2 is a plan view of this apparatus, partially broken away.

In order to fix it in a suitable angular position so that the fins are suitably located below the holes, the container 7 is provided with two dogs such as 15 arranged in fitted crenulations in an annular rib 16 provided around the opening of the cover. These dogs 15 can be noted from FIG. 2 in which one half of the cover has been broken away.

The container is intended to contain physiological salt solution in which the lenses are to bathe during the sterilization; the amount of salt solution to be poured into the container is indicated by a reference mark provided on the inner wall of the container, for instance by a circular shoulder 17 which this wall forms over its inner periphery.

The cell 5, the container 7, and the cover 6 are, in the example shown, made of synthetic material by molding; they are then assembled, first of all by engaging the upper portion of the container below the opening of the cover and force fitting it into the opening and then engaging the cover over the cell. Such arrangements make it possible to obtain a very light and extremely inexpensive unit 1.

We may note furthermore that in order to improve the operation of the apparatus an acid deposit, symbolized at 18, is produced in the cell for instance by allowing a few drops of vinegar to evaporate therein; as will be understood further below, this deposit is intended to acidify the liquid in the cell upon the first sterilizations in order to facilitate the passage of electricity from one electrode to the other.

The feeding of the apparatus with electricity and its mechanical support are assured by the pins 8 which are adapted to be plugged in horizontally; if the user has a wall outlet the jacks of which are in a horizontal plane, he will plug the apparatus in directly and it will thus be in proper position; if he has a vertical wall plug available to him then this plugging will be effected with the use of the connection adapter 14 so that the apparatus is held in the same position. It may be noted that the lightness of the apparatus enables it to be held solely by the wall outlet without danger of damage to the outlet or to the pins.

The adapter 14 is formed very simply of a single-piece body 19 molded of synthetic material in which there have been fastened two male plugs 20 and 20' located in a given plane and two jacks 21 and 21' located in a plane at right angles thereto. Each jack is connected to a plug by an electric wire located within the body 19. Thus the pins 8 and 8' of the apparatus can be plugged in the jacks 21 and 21' of the adapter and, on the opposite side, the plugs 20 and 20' of the adapter are plugged in their turn into the jacks of the wall outlet.

The lenses to be sterilized (indicated symbolically at 22 and 22' in FIG. 1) are placed on the support 2. In the example, the latter has a base 23 of frustoconical shape firmly connected with a grasping rod 24; at its lower part the base 23 has a protruding peripheral rim 25 which serves as support for the lenses. Each of the lenses is thus in contact with two areas of the base located on the same generatrix, a lower area at the level of the rim 25 and an upper area near the rod 24. The base 23 is hollow and provided with several openings such as 26 which, during the sterilization, permit the flow of the physiological salt solution contained in the container 7.

Moreover, the support is provided with a hood 27 comprising on the one hand a frustoconical concave portion adapted to rest against a zone of the convex face of each lens and on the other a neck adapted to slide on the rod 24. This hood locks the lenses in position on the base 23 by the simple effect of its weight; it is in contact with each lens only via a practically punctiform area and does not interfere with the circulation of the physiological salt solution. Of course, the support described has been indicated only by way of example and other embodiments can be contemplated.

The apparatus is completed by a removable cap 3 provided with an internal thread 28 which makes it possible to screw it onto the container. This cap is provided with a stop collar 29 which, in screwed position, prevents the hood 27 from accidentally moving up.

The various parts of the apparatus which has been shown by way of example having now been described its operation as well as the role of each element will be explained with reference to FIGS. 3, 4, 5, 6a, 6b, 7 and 8.

The first operation (FIG. 3) consists in the user pouring physiological salt solution (or more generally any sterilization liquid) into the container by means of a pouring bottle 30; this solution is poured up to the level 17.

The user then places the two lenses to be sterilized on the base of the support 2, secures them in position by putting the hood 27 in place and introduces the assembly into the container 7 (FIG. 4); in this position the lenses are fully bathed within the physiological salt solution. He then screws the cap 3 onto the container; the small collar 29 comes flush with the upper portion of the hood 27 constituting a stop for the latter.

A dose of a conductive liquid is then introduced into the cell of the apparatus through one of the holes 12 in the cover (FIG. 5); this dose is introduced by means of a flexible-wall-dispenser 31 having a capacity equal to the quantity of liquid desired or a integral fraction of said quantity. Said quantity is calculated by the manufacturer to correspond to a suitable time of sterilization. Experience shows that in practice the liquid employed may be water having a medium degree of mineralization, for instance Evian water or, in most regions, ordinary tap water. It should be noted that the introduction of the liquid by means of a dosager eliminates any danger of overflow and therefore even if the apparatus is already connected, any risk of electrocution.

The apparatus is then connected to a wall outlet, either directly in the case of a horizontal outlet 32 (FIG. 6a) or with the use of the adapter 4 in the case of a vertical outlet 33 (FIG. 6b). Such direct connection has essentially three advantages:

simplicity and compactness of the apparatus due to the absence of any connecting cord;

horizontal position of the apparatus is automatically obtained;

impossibility of handling the connected apparatus and carying out dangerous operations such as for instance the filling or cleaning of the apparatus under voltage by means of a faucet (while a connecting cord would permit such dangerous operations).

After connection, with the electrodes bathing in the liquid of the cell (FIG. 7) a current is produced at the center thereof and heats the liquid to the boiling point; the vapor escapes through the holes in the cover. Experience has shown that the acid deposit referred to above facilitates the passage of the current during the first sterilizations; even if this deposit should then disappear; for instance upon the cleaning of the apparatus, the good operation will continue for the entire life of the apparatus.

The physiological salt solution in the container placed on a water bath is heated in its turn without substantial evaporation and produces a sterilization of the lenses which remain at all times in a liquid medium; under the effect of the heat, liquid currents are produced and the structure of the lens support makes it possible for the solution to flow in contact with the entire surface of the lenses, producing complete sterilization.

Gradually the water of the cell evaporates and its level drops; when practically no water is present any longer, the electrodes emerge and the current is automatically disconnected (FIG. 8). The apparatus thus produces a sterilization of a given duration at the end of which its operation is interrupted without any possibility of failure or maladjustment; it can remain connected without danger after the sterilization.

By its very concept, such an apparatus therefore has essential advantages which the known apparatus do not offer; these advantages may be summarized as follows:

automatic shut-off without possible failure;

direct connection to outlet, avoiding the presence of an electric cord and assuring the apparatus minimum size and great convenience in use;

safety in use due to the elimination of any risk of electrocution;

remarkable sterilization of the lenses over their entire surface, under optimum conditions;

simplicity of the structure of the apparatus, imparting it a moderate cost price.

Of course, the present description in no way limits the scope of the invention; the apparatus in accordance with the invention, one embodiment of which has been described above for the sterilizing of optical lenses, can be used to sterilize objects of small size having similar characteristics.

I claim:

1. A portable, compact sterilization device for sterilizing contact lenses comprising, a single cell made of an electrically insulative material and having a bottom as a base and a single cylindrical sidewall upstanding on said bottom defining the interior of said cell, a liquid-tight container having a single cylindrical sidewall and an open neck for receiving therethrough an asepticizing liquid and for providing access into the interior of said container, a removable cover on said cell closing said cell in a fluid-tight manner having at least one opening for introducing a metered volume of an electrically conductive liquid into said cell and to allow vapor to escape therefrom, said cover for said cell further having an opening through which the neck of said container snugly extends, a removable lens-holder insertable into said container through said neck, said lens-holder having means for removably holding a pair of contact lens thereon to be asepticized and an upstanding grip extending out of said neck for inserting the lens-holder into said container and for removing it therefrom, said neck having an external thread, and internally threaded removable cover for threading on to said neck selectively for closing said container in a liquid-tight manner, said container cover having a central region for receiving said grip axially therein and bearing thereon for holding said lens-holder centered and axially seated in said container, a pair of electrical male plug connectors extending outwardly of said cell and spaced for plugging into a standard electrical wall outlet with said sidewall thereof upstanding and the cell and container therein being unsupportd in use otherwise than by said male plug connectors, a pair of spaced electrodes internally of said cell each electrically connected to a respective one of said plug connectors, protective fin means extending from said container having surfaces internally of said cell spaced from and in registry with said opening in said cover to conceal the electrodes and preclude manual insertion of an article into said cell with subsequent contact with said electrodes, and said container being disposed vertically and removable jointly with the cell cover for access into the interior of said cell for selectively cleaning the interior of said cell thoroughly.

2. A portable, compact sterilization device according to claim 1, in which said fin means are integral with said container.

3. A portable, compact sterilization device according to claim 1, in which said bottom has an acid deposit dissolvable in part in said electrically conductive liquid to acidify it.

4. A portable, compact sterilization device according to claim 1, including an adapter having other electrical male plug connectors protruding from a face thereof for connection to a vertically arranged outlet, said adapter having two female jacks for receiving the first-mentioned male plug connectors on an opposite face, said female jacks being located in a plane perpendicular to a plane in which said other male plug connectors are located, and said female jacks being electrically connected to said other electrical male plug connectors.

5. A portable, compact sterilization device according to claim 1, in which said electrodes are disposed adjacent to said bottom.

* * * * *